United States Patent
Takahashi et al.

(10) Patent No.: US 6,391,315 B1
(45) Date of Patent: *May 21, 2002

(54) VACCINE FOR INHIBITING AND PREVENTING INDUCED STAPHYLOCOCCUS INFECTION, ISOLATED ANTIGENS USED THEREIN, AND ISOLATED ANTIBODIES INDUCED THEREBY

(75) Inventors: Takashi Takahashi; Takeji Sasaki, both of Tokyo; Yuzuru Iwai, Chiba; Takashi Hashimoto, Tokyo, all of (JP)

(73) Assignee: Takahashi Hashimoto, Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/509,630

(22) Filed: Jul. 31, 1995

(30) Foreign Application Priority Data

Jul. 29, 1994 (JP) .............................................. 6-178581

(51) Int. Cl.$^7$ ............................................ A61K 39/085

(52) U.S. Cl. .................... 424/243.1; 530/350; 530/412; 530/413; 530/414; 530/418; 424/236.1

(58) Field of Search ........................... 424/236.1, 243.1, 424/234.1; 530/412, 413, 414, 418, 350

(56) References Cited

U.S. PATENT DOCUMENTS

| | | | | |
|---|---|---|---|---|
| 4,075,321 A | * | 2/1978 | Relyveld ..................... | 424/92 |
| 4,327,082 A | * | 4/1982 | Armitage ..................... | 424/92 |
| 4,425,330 A | * | 1/1984 | Norcross et al. ............. | 424/92 |
| 5,034,515 A | | 7/1991 | Proctor | |
| 5,055,455 A | * | 10/1991 | Pier ............................ | 514/54 |
| 5,198,215 A | * | 3/1993 | De Cueninck ............... | 424/92 |
| 5,240,704 A | | 8/1993 | Tsurumizu et al. | |

FOREIGN PATENT DOCUMENTS

| | | |
|---|---|---|
| EP | 0 094 997 | 11/1983 |
| EP | 0 163 623 | 12/1985 |
| WO | WO 93/17044 | 9/1993 |
| WO | 9422474 | * 10/1994 |

OTHER PUBLICATIONS

Braude et al. Infectious Disease & Medical Microbiology, $2^{nd}$ ed, 1986. pp. 236–253.*
Rysanek, et al. 1988. Monatshefte fur veterinaermedizin. 43: 58–60.*
Hisanori et al. JICST Accession No: 94A0926646.*
A. Cheung et al., "Surface Proteins of *Staphylococcus aureus*", Reviews of Infectious Diseases, Supplement 2, vol. 10, Jul.–Aug. 1988, pp. 351–355.

(List continued on next page.)

Primary Examiner—Jennifer E. Graser
(74) Attorney, Agent, or Firm—Young & Thompson

(57) ABSTRACT

An antigenic composition is derived from surface extracted protein of cell wall surfaces and the culture supernatant extract of Staphylococci. The strain is highly virulent and β hemolytic on blood agar plate. They are mixed and purified by ion exchange and gel filtration column chromatography. This preparation method can be used in all Gram-positive bacilli. The antigens, having molecular weight of about 10,000–70,000 are certain kinds of glycoprotein comprising proteins (ca. 10–20%) and carbohydrates (ca. 75–90%). They are extracted from the cells with the use of a hypertonic buffer solution of pH 6.5–8.5 at a temperature below the denaturing point of the antigenic protein, and are salted out with ammonium sulfate (ca. 65–85%). The culture supernatant is extracted in the same way by salting out with ammonium sulfate (ca. 65–85%). The antigen fraction from both cell wall and culture supernatant is obtained in such an operation. The antigen can be used as a preparation antigen to Staphylococcus antigen. Namely, the antibody obtained from mammal and avian immunized by this antigen can be used to treat the above-described infections. The composition containing the antibody provides a preventive effect.

14 Claims, 1 Drawing Sheet

OTHER PUBLICATIONS

L. Sutra et al., "Virulence factors involved in the pathogenesis of bovine intramammary infections due to *Staphylococcus aureus*", J. Med. Microbiol., 1994, vol. 40, pp. 79–89.

C. Adlam et al., "Effect of Immunization with Highly Purified Alpha– and Beta–Toxins on Staphylococcal Mastitis in Rabbits", Infection and Immunity, Aug. 1977, pp. 250–256.

"Treatment of demyelinating disease e.g. multiple sclerosis by administration of detoxified, immunogenically active *Staphylococcus aureus* α–toxin; vaccine preparation", Oct. 1986, US 4,615,884.

D. Watson, "Vaccination against experimental staphylococcal mastitis in ewes", Research in Veterinary Science, 1988, vol. 45, pp. 16–21.

S. Morse, "Staphylococci and Other Micrococci", Bacterial and Mycotic Infections of Man, p. 412.

T. Foster, "Potential for vaccination against infections caused by Staphylococcus aureaus", Vaccine, Apr. 1991, vol. 9, pp. 221–227.

* cited by examiner

VACCINE FOR INHIBITING AND PREVENTING INDUCED STAPHYLOCOCCUS INFECTION, ISOLATED ANTIGENS USED THEREIN, AND ISOLATED ANTIBODIES INDUCED THEREBY

BACKGROUND OF THE INVENTION

1. Field of the Invention

The present invention relates to a vaccine, as well as isolated antigens and antibodies constituting a composition for inhibiting and preventing induced Staphylococcus infection. More particularly the present invention concerns a vaccine for prevent Staphylococcus infection, its prevention by antibody, therapeutic antibodies and production thereof.

2. Description of Related Art

In the past years, an inactivated vaccine comprising hemolysin and coagulase extracted from a culture medium of *Staphylococcus aureus* was used for treatment of Staphylococcus infections. However, since newly developed antibiotics have also been used for treating Staphylococcus infections, the need for vaccine treatment of Staphylococcus infection has been reduced, and finally the vaccine was no longer used and consigned to lasting oblivion. No development of or ideas for vaccines in this connection have recently appeared. The vaccine for Staphylococcus in the past was not specified as to the effective component, and thus the incomplete combination of purification and undetermined effective component rendered its preventive effect unclear.

Staphylococcus is a Gram-positive bacterium and exists as a normal inhabitant, i.e. indigenous bacterium, of human skin and mucous membrane. Although most strains produce biologically active toxins and enzymes, little is known yet concerning the pathogenesis of Staphylococcal disease which has been markedly aroused in recent years by an apparently increasing incidence of severe illness, particularly in hospital environments where many strains are insensitive to the antimicrobial agents which have so successfully prevented disease mortality by other pyrogenic cocci (*Bacterial and Mycotic Infections of Man*, 4th Ed, 1991). On the other hand, conventional Staphylococci vaccines have been tried, namely an autogenous vaccine. Although some doctors have tried this vaccine, its efficacy is yet unclear, because the strain has to be isolated from the patient and inactivated by formalin to prepare the vaccine, and the vaccine thus prepared has to be injected over a long period. This vaccination may inhibit the secondary infection in humans, caused by Staphylococci.

For animals, there is a vaccine in which the whole cells and culture broth are separately inactivated with formalin, and thereafter mixed. This vaccine is to prevent mastitis of animals (Watson D. L., *Res. Vet. Sci.;* 45, 16–21, 1988). For mastitis, the other vaccines are based on highly purified α and β toxin (*Infect. Immun.*, 17, 250–256, 1977) and fibronectin-binding protein (FnBP-A) (*EUR*, 294–349, 1988, *Vaccine*, 12, 11, 918–922, 1994). It is also known to use a subunit vaccine having components from surface proteins and polysaccharides (T. J. Foster, *Vaccine* 9, 4, 221–227, 1991), and synthetic ST enterotoxin comprising 4n to 18n amino acids is said to be useful for inducing in vivo antibodies (U.S. Pat. No. 4,499,080). But these are not vaccines for Staphylococcus infection due to the use of only general vaccine antibody inducing agents.

SUMMARY OF THE INVENTION

In the present invention, a strong β hemolytic strain, which is a methicillin resistant strain (MRSA in particular) isolated from patients, is cultured in anaerocolumbia agar with rabbit blood (BBL Japan) by the BBL anaerobic jar system. This strain produces component TSST-1 and strong β hemolysin. After centrifugation of the cultured broth, the supernatant is filtered, ammonium sulfate is added to a concentration of about 65–85% and the resulting precipitate is preserved for later use. The whole cells are immediately suspended in hypertonic buffer solution and are stirred at a temperature below the denaturing point of protein. After centrifugation, ammonium sulphate is added to the cell extract and the resulting precipitate is mixed with the supernatant precipitate. The mixed solution is treated by ion exchange column chromatography to eliminate impurities. The fraction having molecular weight of about 10,000–70,000 is obtained by gel filtration. The main constituents are TSST-1, hemolysin, and enterotoxin, however, this fraction contains neither endotoxin nor whole cells.

The inactivated vaccine of the present invention is thus based in part on the discovery that the antigens have been isolated by mixing the cell surface extract with the supernatant extract. In addition, the preferred strain is a methicillin resistant bacterium isolated from patients showing excellent antigenic activity; moreover, the antigen derived is extracted from the cell wall using a hypertonic buffer solution under mild conditions, and further the specific antigen includes super antigen, major enterotoxins, and the like. The same enterotoxins, for example A, B and C, are produced not only by *Staphylococcus aureus* but also by other species of Staphylococcus. The vaccine derived from the other species contains similar compositions as *Staphylococcus aureus* and may be cross-reactive, and the antibody possesses anti-superantigen neutralizing antibody.

The present invention is therefore directed to a process for producing an antigen preparation for inhibiting or preventing induced Staphylococcal infections in humans, a vaccine containing such an antigen or antigens, and a process for producing antibodies for inhibiting or preventing human and animal infections induced by Staphylococcal compositions containing such antibodies. According to a feature of the present invention, a process for isolating two antigens for preventing or inhibiting human staphylococcal infection comprises separating the whole cells of at least one strain of Staphylococcus from cultured broth, extracting at least some antigens of the cell surface and at least some exotoxin antigens and fractionating the resultant antigen from the extract thus obtained. This vaccine is characterized by containing superantigen (for example TSST-1) and an antibody possessing superantigen neutralizing activity.

DETAILED DESCRIPTION OF PREFERRED EMBODIMENTS

Figure 1:
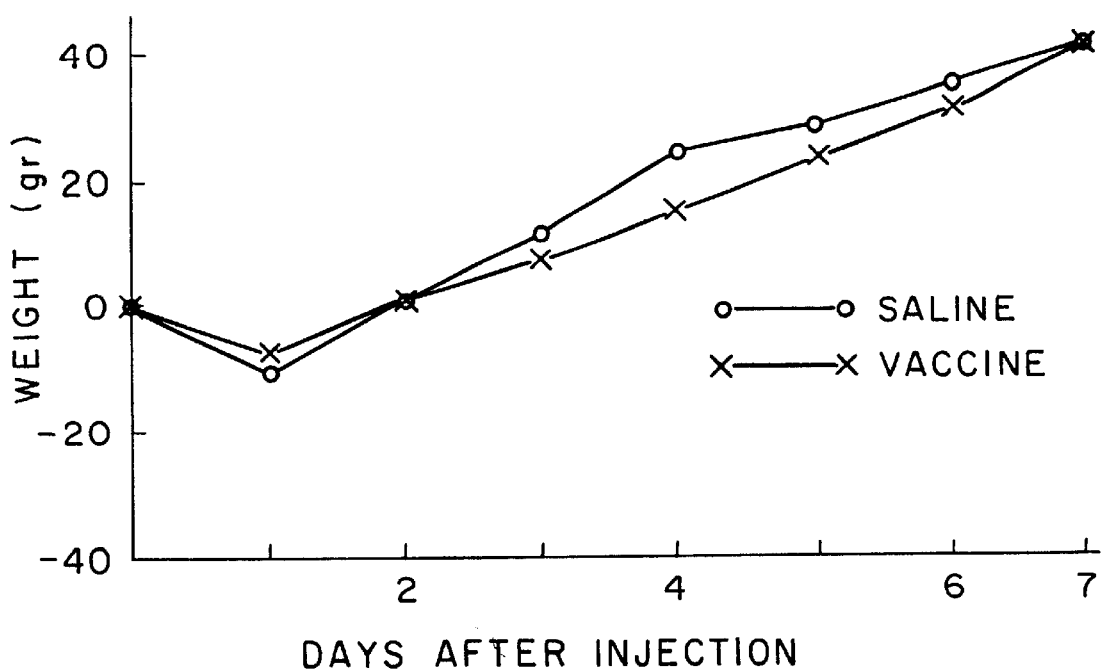
FIG. 1 is test showing no abnormal toxicity of the present vaccines.

For the purpose of the present invention, antigens derived from both cell surface extracts and cultured broth are mixed. The mixed solution is treated by ion exchange chromatography and gel filtration chromatography to obtain the effective fraction. The fraction which is useful as a vaccine for humans and animals is free of endotoxin and whole cells. The preparation method of this vaccine can be applied to all Gram-positive bacteria, although *Staphylococcus aureus* is most important. These bacteria may be used singly or in combination. Various mutant strains thereof may also be used for the purpose of the present invention insofar as they are capable of inducing opportunistic infections. Accordingly, if desired, the vaccine of the present invention comprises two more component antigens originating from virulent microorganisms of other species possessing superantigens. In the examples and experiments described hereinafter, *Staphylococcus aureus* KT-472 is used. This strain has been deposited at American Type Culture Collection, which is located at 10801 University Boulevard, Manassas, Va. 20110 on Jul. 24, 1995 and assigned Deposit No. ATCC 55697. When this strain is cultured, for example by using blood agar plate, a strong hemolysin or coagulase content is produced.

The biochemical characteristics of the strain KT-472 are as follows:
1) Morphology: cocci, Gram-positive, 0.8–1.0 μm
2) Growth property: aerobic (facultative anaerobic)
3) Growth on various media:
    a) Staphylococcus agar 110 medium (commercial medium) (pH about 7.2–7.4) Colonies formed are smooth, small, yellow or pale orange color.
    b) Trypticase soy agar (commercial medium) (pH 7.2–7.4) Colonies are uniform, round and have smooth surface.
    c) Brain hear infusion broth (commercial medium) (pH 7.2–7.4) Growth uniformity, in the medium.
4) Hemolysis on blood agar: rabbit, sheep, goat and horse
5) Coagulase production: positive, type II
6) Enterotoxin production: A, B and C, TSST-1, Hemolysin
7) Growth range: pH 4.8–9.4, temperature 10–45° C.
8) Decomposition of sugar: positive (+) for sucrose, D-mannitol, D-mannose, lactose, D-trehalose, D-galactose, D-fructose; negative (1) for arabinose, cellobiose, fucose, xylose, elegitose, salicine, rhafinose.
9) Miscellaneous: coagulase (+), motility (−)
10) Drug resistant: methicillin Physiological characteristics of the extracted antigen are as follows:

1) Color and smell: pale yellow, no specific smell.
2) Toxicity: 10 μg protein N/0.1 ml injected intraperitoneally in mice (four weeks age); all dead within 3 hours.
3) Stability: denatured at room temperature after ten days, stable at 4–8° C. for about six months, stable below −20° C., inactivated at 100° C. heating for 60 mins.
4) Solubility: soluble in water or buffer solution.
5) pH: dried preparations show weak acidity.
6) Molecular weight: in 7.5% polyacrylamide gel (SDS PAGE):
    electrophoresis: 10,000–70,000
    main component: 20,000–40,000
7) Major component: enterotoxin A, B and C, TSST-1, hemolysin.

It is possible, if necessary, to add appropriate adjuvant to the antigen, such as aluminum phosphate, aluminum hydroxide, muramyldipeptide and general oil adjuvant to obtain an antigen solution suitable for immunizing humans and animals. Dosage of the resultant vaccine solution containing antigen is usually 2–50 μg protein N per adult (body weight of about 50 kg), if desired, preferably 2–10 μg protein N. The mixture of the surface extract and cultured broth prepared by this process is preferably purified to the fraction of molecular weight 10,000–170,000, and is further preferably purified to the fraction of molecular weight 10,000–70,000. The purified fraction is inactivated by formalin or the like. Staphylococcal infection can be largely prevented and inhibited by this antigen. The resultant antibodies can also be used for medical treatment and the composition containing the antigen and antibody is expected to have preventive effect.

Microorganisms, which can be used as a source of cell surface component antigens and culture broth extracts of the present invention, can be cultured in a conventional manner for culturing various strains of corresponding species. Culturing may be effected by using either synthetic or organic media, and liquid media may be preferred for mass production. For example, the culturing may usually be effected at a temperature of 25–40° C. (preferably at about 36° C.) and at pH of 5.0–8.5 (preferably at about 7.2) under slightly anaerobic conditions for 20–70 hours. Media for culturing the microorganism exemplified as follows:

Medium A: Trypticase soy broth [commercial medium]

Medium B: Brain hear infusion [commercial medium]

Medium A and B are preferred for *Staphylococcus aureus* KT-472, and preferred methods for the preparation of vaccine of the present invention are illustrated as follows.

Microorganisms are cultured at 30–37° C., pH 6.5–8.5 for 18–48 hours to obtain seed culture. The seed culture is then transferred to a main medium of the same composition, and cultured for 24–72 hours under the same conditions. After completion of culturing, the cells are separated from the cultured broth, for example, by centrifugation (8,000 rpm/30 min.) and suspended immediately in a suitable solution well known in the art such as 0.01M–0.05M tris-HCl buffer containing 0.5M–2M NaCl (pH 6.5–8.5), or 0.01M–1M phosphate buffer containing 0.5M–2M NaCl (pH 6.5–8.0).

A suitable non-ionic surfactant, such as triton X-100 (0.01–0.001% w/v) (commercial product of Rohm and Hass, U.S.A.) may, if desired, be added. The cell suspension is treated by stirring for 48–112 hours at a temperature below the denaturing point of antigenic protein with sonication of, for example, 10–20 KHz/2–5 min. to extract the desired surface antigen. After stirring, the sonicated cell suspension is treated, for example, by centrifugation (8,000 rpm/30 min.)

The supernatant is salted out with, for example, 50–85% ammonium sulphate to obtain cell surface extract. The supernatant of the cultured broth separated from the cells is salted out with, for example, 50–85% ammonium sulphate to obtain the cultured broth extract. Both extracts from cell surface and cultured broth, containing desired antigen, are then mixed, and fractionated and purified in a conventional manner, for example, by column chromatography, isoelectric point precipitation or partition precipitation using a cold solvent such as ethanol. If desired, the resultant solution is treated with a suitable inactivating agent such as formalin (0.1–0.8% w/v), followed by dialysis against a similar buffer solution to remove formalin.

The solution containing the antigen is diluted with a suitable buffer solution such as 0.01–0.1M phosphate buffer saline (pH 6.2–7.2) to adjust the protein N concentration to 2–50 μg protein N/ml. To the dilute solution is added aluminum hydroxide as adjuvant at final concentration of aluminum about 100–200 μg/ml to adsorb the antigen. Muramyldipeptide, may, if desired, be used in place of aluminum hydroxide. To the mixture is added a suitable antiseptic reagent such as thimerosal (0.05–0.01% w/v) to obtain an antigen solution of the present invention. In the cell surface extracts, instead of treatment with ultrasound, it is also possible to add ammonium sulphate of about 50–85% saturation (for example 75%) with stirring to dissolve ammonium sulphate. The supernatant is then discarded.

The precipitate is dissolved in a suitable buffer solution such as 0.05–0.5M phosphate buffer solution (pH about 6.5–8.0) followed by dialysis in the buffer solution at cold temperature. The residual solution is centrifuged (e.g. 8,000 rpm/30 min.) and the resultant extracted solution is fractionated and purified in a similar manner as described above. In order to prevent denaturing the antigen of the present invention, the above-mentioned procedure may advantageously be carried out at cold temperatures, for example, below 10° C. The vaccine thus prepared may be preserved over an extended period of time. The dosage of vaccine of the present invention may vary, depending upon various factors, for example, types and symptoms of the Staphylococcal infection which is the target of administration. However, it is usually possible to administer the vaccine to humans at daily dose of, for example, 0.1 to 0.2 ml by subcutaneous or intramuscular injection. This dosage may also be effective for immunization purposes.

It is also possible, if desired, to administer components of the vaccine of present invention consecutively. It is possible to inhibit infection by wild strains or at least by the corresponding species in humans and animals. If desired, it is also possible to immunize a mammal or avian with the vaccine of present invention to produce an immunological antibody, and the administration can be carried out using standard animals in a conventional manner, such that the resultant antibody is reproducible.

Test of the Vaccine

Each vaccine prepared by the method of Example 1 infra was subjected to staining tests, bacterial culturing tests and acute abnormal toxicity tests, all according to "Minimum Requirements of General Tests for Biologics (1994)" issued by the Ministry of Welfare of the Japanese government, in the following manner. Nothing unusual was noted.

(1) Staining test:

A sample vaccine (about 10 ml) was put in a test tube and centrifuged (about 2,000 g/30 mins.) to form precipitate. Then, Gram's stain was applied to the sample for staining test. The sample was observed microscopically (×1,000). No microorganisms were observed.

(2) Bacterial negative test:

A sample vaccine (0.2 ml) was divided into two equal portions. Each fraction was cultured for ten days at 30–32° C. using thioglycolic acid medium (commercial product of Difco, U.S.A.) Nothing unusual was noted on the 2nd, 3rd, 7th, 10th and 14th days after starting the culture.

(3) Test for abnormal acute toxicity:

Five mice of three weeks age were abdominally injected with a sample vaccine (each 0.5 ml). Each animal was observed for subsequent seven days. No unusual toxicity was noted.

EXAMPLES

In the following non-limiting examples for illustrating the invention, culturing was effected at a temperature of 30–37° C. under slight anaerobic conditions and the test animals, ddY mice (Clean, SPF) (SLC Japan) each group consisting of 10 to 60 animals, or guinea pig (about 200 g), were used unless otherwise specified.

Example 1

Preparation of Vaccine

Staphylococcus aureus KT-472 (isolated from MRSA patient) was cultured for 24 hours by using anaerocolumbia agar with rabbit red blood (BBL Japan) by the BBL culturing jar system to obtain seed. The seed was transferred to preculture medium A (100 ml) and cultured for 8 hours under similar conditions as noted above. The seed culture was transferred to a main culture medium of the same composition (10,000 ml) and cultured for 24 hours under similar conditions. Culture broth was centrifuged to separate the broth from cells. Solid ammonium sulphate was added to the cultured supernatant broth at 85% saturation. Separately, the cells were suspended in a 0.01M phosphate buffer containing 1M NaCl (pH 8.0, 100 ml) and stirred for 72 hours at low temperature, and cell debris was removed by centrifugation.

Ammonium sulphate was added to the cell-free supernatant broth at 85% saturation, and stirred at 4° C. for a further 24 hours. The precipitates of the extracts of supernatant and cells were collected, respectively, by centrifugation (8,000 rpm/30 mins.) Then the precipitates were mixed and dissolved in a 0.05M tris-HCl buffer (100 ml, pH 8.0) and were subjected to dialysis against a similar buffer solution, and centrifuged (12,000 rpm/20 mins.) to remove impurities. The resultant supernatant (about 120 ml) contained proteinaceous nitrogen at about 2–3 mg/ml and was put into a visking tube Union Carbide, U.S.A.) to concentrate the amount ten-fold.

The combined cell extracts and supernatant were eluted by means of ion exchange column chromatography (Whatman DE-52 60 g, U.S.A.) with the solution of 0.05M tris-HCl buffer containing 0.09M NaCl (total elution volume 2,100 ml) for removal of impurities; and the volume was concentrated 1,000-fold as described above. That is, the eluate was concentrated by visking tube (about 3 ml). The eluate was then gel filtrated with Sephacryl-200 (Pharmacia, Sweden) and eluted with 0.5M NaCl 0.01M phosphate buffer solution (pH 7.2). Fractions were collected by monitoring at 280 nm. The fractions of molecular weight (10,000–70,000) were collected. The combined active fractions exhibited hemolytic activity on rabbit red blood cell at a dilution ratio of 1:1024. The active principal was inactivated by contact with 0.3% formalin for 10 weeks at 4° C. On each occasion, the fractions were diluted with 0.01M phosphate buffer saline (pH 7.0) to give a concentration of proteinaceous nitrogen of 5 to 50 $\mu$g/ml. Inactivation was carried out in the same manner as above. After removal of formalin by dialysis against the same buffer solution, aluminum hydroxide gel was added to final concentration of 20 $\mu$g/ml to adsorb the antigens. The pH of combined antigen solution was adjusted to 6.5 and thimerosal, an antiseptic agent, was added to the solution.

Example 2

Inactivation Test by Intradermal Reaction in Rabbits

About 10 $\mu$g of protein N of the antigen obtained in Example 1 were injected intracutaneously into rabbits (weighing about 2 kg, New Zealand white, Gokita, Japan). The injected rabbits died within 15 hours. Intracutaneous injection of 200 $\mu$g protein-aceous nitrogen of the inactivated antigen in rabbits did not cause death, accordingly the intradermal reaction of the inactivated antigen was negative.

Example 3

Cytotoxic Effect on Vero Cells

Vero cells were grown in MEM (Gibco, U.S.A.) to which was added 5% fetal calf serum via a 96 hole microplate. The dilution series of the antigen of Example 1 before inactivation (inactivated antigen), at 25 $\mu$l increments, were added thereto. Cells were incubated for five days at 37° C., and cell degeneration was observed. The results are shown in Table 1. Inactivated antigen showed no cytotoxic effect on Vero cells.

TABLE 1

Cytotoxic Effect on Vero Cells

| Antigen/dilution | origin | × 10 | × 100 | × 1,000 | × 10,000 |
|---|---|---|---|---|---|
| Before inactivation | + | + | + | + | + |
| Inactivated | ± | − | − | − | − |

Example 4

Lethal Dose Test of the Prepared Antigen

Saline solution of the antigen before inactivation, containing 10 to 100 μg protein N prepared in Example 1, were injected intraperitoneally into ddY mice (SPF, four weeks age), 10 mice in each group, and the condition of the mice was observed for seven days. All the mice administered with 100–50 μg/0.1 Nml mouse died within 3 hours after injection. The other groups died within 20 hours after injection. The results are shown in Table 2.

TABLE 2

Lethal Dose Test of the Prepared Antigen

| protein (μg/0.1 Nml mouse) | no. of animals | mortality | survivor (%) |
|---|---|---|---|
| 100 | 10 | 10 | 0 |
| 75 | 10 | 10 | 0 |
| 50 | 10 | 10 | 0 |
| 20 | 10 | 10 | 0 |
| 10 | 10 | 3 | 70 |

Example 5

Virulence Test of the Strains Used in Experiments

Lethal dose tests were conducted using the strains of *Staphylococcus aureus*, TSST-1 producing strain A and TSST-1 non-producing strain B, isolated from patients. The strains were cultured on anaerocolumbia agar with rabbit blood agar (BBL Japan) in a BBL anaerobic culture jar system for 24 hours at 37° C. Ten-fold dilution series of cell suspension were prepared. Diluted cell suspensions of $10^{10}$ cfu/ml to $10^8$ cfu/ml were injected, 0.1 ml/mouse, intraperitoneally into ddY mice (four weeks old). Lethality was observed for 14 days after injection. Results are shown in Tables 3 and 4. As can be seen, 80% of mice injected intraperitoneally with strain (A) $10^8$ cfu/mouse died, and over 50% of mice injected i.p. with strain (B) $10^8$ cfu/mouse died.

TABLE 3

Virulence Test for the Strains

| number of cells | number of mice | number of death | survivor (%) |
|---|---|---|---|
| $4 \times 10^{10}$ cfu | 10 | 10 | 0 |
| $4 \times 10^9$ cfu | 10 | 10 | 0 |
| $4 \times 10^8$ cfu | 10 | 8 | 20 |

Strain (A) TSST-1 producing strain was used (i.p. injection).

TABLE 4

| number of cells | number of mice | number of death | survivor (%) |
|---|---|---|---|
| $3 \times 10^{10}$ cfu | 10 | 10 | 0 |
| $3 \times 10^9$ cfu | 10 | 10 | 0 |
| $3 \times 10^8$ cfu | 10 | 6 | 40 |

Strain (B) (TSST-1 non-producing strain) was used (IP injection).

Example 6

Lethal Dose of Prepared Antigen

Solutions containing 2.5, 5 and 10 μg protein N of vaccine obtained in Example 1 was prepared, respectively, and was adsorbed onto aluminum hydroxide adjuvant (200 μg/ml). 0.2 ml vaccine was subcutaneously injected in 120 mice (ddy, SPF, 4 weeks age, SLC, Japan). After three weeks, the mice, ten mice in each group, were challenged by toxin and viable cells. The protein in the challenged toxin was adjusted to 20 μg/ml, and 0.1 ml thereof was intraperitoneally injected. Viable cells were diluted with Hemacell Hoechst, Germany) and the solution of 10 cfu/ml to $10^{10}$ cfu/ml were intraperitoneally injected, and the condition of the mice was observed for 14 days. The results are shown in Tables 5, 6 and 7. The results indicated that in the toxin-challenged group, 100% survived when immunized with 10 μg protein N antigen. In the viable cells of TSST-1 producing strain challenged group, 100% of mice survived when immunized with 2.5 μg protein N antigen, and in the cells of TSST-1 non-producing strain challenged group, 70% of mice survived when immunized with 5 μg protein N antigen.

Blood was collected from both the mice surviving after challenge and the mice immunized without challenge, and was used in the following test as antibody.

TABLE 5

Lethal Dose of the Prepared Antigen:
Challenged with Antigen Before Inactivation

| vaccine (protein N μg/mouse) | number of mice | number of death | survivor (%) |
|---|---|---|---|
| 10 | 10 | 0 | 100 |
| 5 | 10 | 2 | 80 |
| 2.5 | 10 | 4 | 60 |
| control | 10 | 10 | 0 |

Toxin (20 μg/0.1 ml) was injected IP.

TABLE 6

Challenged with TSST-1 Producing Cells

| vaccine (protein N μg/mouse) | number of mice | number of death | survivor (%) |
|---|---|---|---|
| 10 | 10 | 0 | 100 |
| 5 | 10 | 0 | 100 |
| 2.5 | 10 | 0 | 100 |
| control | 10 | 9 | 10 |

Viable cells (5×10⁸ cfu/mice) were injected IP.

TABLE 7

Challenged with Non TSST-1 Producing Cells

| vaccine (protein N μg/mouse) | number of mice | number of death | survivor (%) |
|---|---|---|---|
| 10 | 10 | 3 | 70 |
| 5 | 10 | 3 | 70 |
| 2.5 | 10 | 6 | 40 |
| control | 10 | 9 | 90 |

Viable cells (4×10⁹ cfu/mice) were injected IP.

Example 7

Antibody Production Test (1) Agglutination Antibody Titer to Viable Cells

A suspension of viable cells (TSST-1 producing strain) was prepared with 0.01M phosphate buffer saline containing 0.1% w/v albumin. Immunized serum (25 ml) was pipetted in the microplate, and a series of two-fold dilution in microplate with the same buffer hereinabove was prepared. An equal volume of the viable cell suspension was added thereto and mixed. The mixture was incubated at 37° C. for two hours and then was left at 4° C. overnight, whereafter agglutination antibody titers were measured. The antibody titer was assayed as 1:16 in 10 μg protein N immunized group, and 1:8 in 5 μg protein N immunized group. Accordingly, though antibody titer is not so high, the antibody titer is increased. Control shows negative titer. The results are shown in Table 8.

TABLE 8

Agglutination Antibody to Viable Cells

| Vaccine (protein N/mouse) | number of mice | antibody titer | ep | sp |
|---|---|---|---|---|
| 10 | 10 | 1:16 | 1:4 | 1:8 |
| 5 | 10 | 1:8 | (—) | 1:4 |
| control | 10 | (—) | (—) | (1) | ep: *Staphylococcus epidermidis*, sp: *Staphylococcus saprophiticus*

Example 8

Antibody Production Test (2) Neutralization to Hemolysin

Antigen before inactivation titered to 2¹⁴/ml was diluted to 2³/ml. Immunized serum was prepared in the series of two-fold dilution on microplate by using the same buffer solution as described in Example 7. An equal amount of 2³/ml antigen was added to the corresponding serum and mixed. The mixture was allowed to sensitize at 37° C. for two hours. An equal volume of 2% rabbit red blood cells was added to the corresponding serum and mixed together. The mixture was allowed to react at 37° C. for one hour. Hemolysin neutralizing antibody titer is shown in 1:8 to 1:16 in 5 μg protein N immunized group and 1:8 to 1:16 in 10 μg protein N immunized group. Hemolysin neutralizing antibody titer in survived mice after challenging is shown in 1:64. The results are shown in Table 9.

TABLE 9

Hemolysin Neutralization Titer

| vaccine (protein N/mouse) | only immunized | survived |
|---|---|---|
| 10 | 1:8~16 | 1:64 |
| 5 | 1:8~16 | 1:64 |
| control | (—) | |

Example 9

Neutralizing Titer of Immunized Serum with Vaccine to TSST-1

Toxin TSST-1'(Toxin Technology, U.S.A., 1 mg/ml) was diluted to a titer of 2³/ml (1:8). Immunized serum was prepared in the series of two-fold dilution on microplate with buffer as described in the above Example 7. An equal volume of TSST-1 antigen (2³/ml) was added to the corresponding serum and mixed. The mixture was allowed to sensitize at 37° C. for two hours and left at room temperature overnight, whereafter neutralizing antibody was measured by using TST-RPLA (Seiken) (Denka Seiken, Japan). The antibody titer was shown in dilution of 1:8 in mice surviving after challenging with toxin. The results are shown in Table 10.

TABLE 10

Neutralizing Titer to TSST-1

| weeks after immunized | vaccine(protein N/mouse) | antibody |
|---|---|---|
| 3 | 10 | 1:8 |
| 1 | 10 | 1:8 |
| control | saline | (—) |

Example 10

Infection Inhibiting Test by Passive Immunization

Antibody was prepared by subcutaneously injecting antigen (100 μg protein N) with emulsified Freund incomplete adjuvant (1:1) into rabbits. The antigen (100 μg protein N) was injected into rabbits at intervals of 2, 4 and 8 weeks, respectively. After 9 weeks, blood was collected from the carotid artery. The immunized serum was diluted serially from 1:512 to 1:32 with 0.01 M phosphate buffer saline. An equal volume of corresponding antigen (hemolysin titer 1:128) was mixed and allowed to stand for sensitization at 37° C. for one hour. Sensitized solutions 0.2 ml each were injected in mice (ddY, 4 weeks age) intraperitoneally. The toxin solution (hemolysin titer 1:128/0.1 ml) was injected into mice as control. Each animal was observed for the subsequent 7 days. All the mice in the control group died within one day whereas more than 60% of mice in the neutralized serum group survived at the dilution of serum 1:32. The findings herein-above clearly indicate that the anti-serum neutralizes toxin in serum. The possibility of medical treatment was clearly provided. The results are shown in Table 11.

TABLE 11

Infection Inhibition by Passive Immunization with Anti-serum

| antibody titer | number of mice | number of death | suvivor (%) |
|---|---|---|---|
| X512 | 10 | 0 | 100 |
| 256 | 10 | 0 | 100 |
| 128 | 10 | 0 | 100 |
| 64 | 10 | 4 | 100 |
| 32 | 10 | 4 | 60 |
| control | 10 | 10 | 0 |

Example 11

Infection Inhibition Test for Viable Cells Challenged in Mice by Passive Immunization Viable cells grown on anaerocolumbia agar with rabbit blood agar (BBL Japan) at 37° C. overnight by the BBL anaerobic jar system, were collected. Viable cells ($10^{10}$ cfu/ml) were diluted to $10^9$ cfu/0.1 ml with Hemacell (Hoechst, Germany). Cells were sensitized with corresponding antiserum in the dilution from 1:16 to 1:256, respectively, and allowed to stand at 37° C. for one hour. Sensitized cells in the solution were injected in mice intraperitoneally. The cells ($10^9$ cfu/0.1 ml) were injected intraperitoneally as a control. Each animal was observed for the subsequent two weeks. All mice in the control group died within three days. More than 40% of the animals in the sensitized serum group survived at the dilution of the titer of 1:16. The efficacy of sensitized serum on the medical treatments was clearly proved. The results are shown in Table 12.

TABLE 12

Infection Inhibiting Test by Passive Immunization with Viable Cells

| antibody titer | number of mice | number of death | suvivor (%) |
|---|---|---|---|
| X256 | 10 | 6 | 40 |
| 128 | 10 | 8 | 20 |
| 64 | 10 | 8 | 20 |
| 32 | 10 | 8 | 20 |
| control | 10 | 10 | 0 |

Viable cells (10 $LD_{50}$cfu/mice) were injected into IP. Control: all dead within 3 days.

Example 12

Test for Proving No Abnormal Toxicity

Antigen (10 μg protein N/ml) 5 ml per guinea pig (about 300 g), was injected intraperitoneally in 60 animals to examine abnormal toxicity in accordance with minimum requirement for biological product standard of Japan. The results indicated that the animals showed no noticeable decrease in body weight as compared with the control. The results are shown in FIG. 1.

Example 13

Endotoxin Assay

Endotoxin was assayed by toxinocolor system II (Seikagaku Kogyo, Japan). The original antigen (not diluted) showed assaying result of 25 pcg. Accordingly, endotoxin of the antigen is below the lower limit of rabbit feber (50 pcg).

Although the present invention has been described in connection with various preferred embodiments thereof, it will be appreciated that these embodiments are provided solely for purposes of illustration, and should not be construed as limiting the scope of the invention. Other embodiments and applications of the invention will be readily apparent to those skilled in the art from reading the present specification and practicing the techniques described herein, without departing whatsoever from the scope and spirit of the appended claims.

What is claimed is:

1. An antigenic composition prepared by culturing a broth of a pathogenic bacterium selected from the group consisting of *Staphylococcus aureus* and *Staphylococcus epidermidis*, centrifuging the cultured broth, separating a supernatant from whole cells within the cultured broth, precipitating components separately from the supernatant and said whole cells and removing the precipitated components from residual components of the supernatant and whole cells, preparing a mixed solution that is substantially free of said residual components by combining precipitates from said whole cells and said supernatant, and subjecting said mixed solution to column chromatography to isolate said antigenic composition as a rabbit red blood cell hemolysis positive fraction consisting of components having molecular weight of about 10,000–70,000, said composition comprising as main constituents TSST-1, hemolysin, and enterotoxin, said antigenic composition further being free of endotoxin and whole cells.

2. The composition of claim 1 comprising the following physiological properties:
   1) Color and smell: pale yellow, no specific smell,
   2) Toxicity: 10 μg protein N/0.1 ml injected intraperitoneally in mice (four weeks old); and dead within-3 hours,
   3) Stability: denatures at room temperature after ten days, stable at 4–8° C. for about six months, stable below −20° C., inactivated by heating at 100° C. for 60 mins,
   4) Solubility: soluble in water or buffer solution,
   5) pH: dried preparations show weak acidity,
   6) Molecular weight: in 7.5% polyacrylamide gel (SDS PAGE):
      electrophoresis: 10,000–70,000
      main component: 20,000–40,000 and
   7) Major component: enterotoxin A, B, and C, TSST-1, hemolysin.

3. A vaccine for preventing and inhibiting Staphylococcal infection, comprising the composition of claim 1.

4. The vaccine of claim 3 further comprising an immunological additive.

5. The vaccine of claim 3 further comprising an additive of aluminum salt, muramyldipeptide or oil adjuvant.

6. The composition of claim 1, wherein said composition is inactivated with formalin.

7. The composition of claim 1, wherein said *Staphylococcus aureus* is methicillin-resistant *Staphylococcus aureus* (MRSA).

8. The composition of claim 1, wherein said enterotoxin is enterotoxin A, B and C.

9. A process for preparing an antigenic composition, comprising the steps of culturing a broth of a pathogenic bacterium selected from the group consisting of *Staphylococcus aureus* and *Staphylococcus epidermidis*, centrifuging the cultured broth, separating a supernatant from whole cells within the cultured broth, precipitating components separately from the supernatant and said whole cells and removing the precipitated components from residual components of the supernatant and whole cells, preparing a mixed solution that is substantially free of said residual components by combining precipitates from said whole cells and said supernatant, and subjecting said mixed solution to column chromatography to isolate said antigenic composition as a rabbit red blood cell hemolysis positive fraction consisting of components having molecular weight of about 10,000–70,000, said